(12) United States Patent
Seo et al.

(10) Patent No.: US 8,263,693 B2
(45) Date of Patent: Sep. 11, 2012

(54) FLAME RETARDANT RESIN COMPOSITION HAVING GOOD IMPACT STRENGTH AND HIGH MELT FLOW INDEX

(75) Inventors: You-seok Seo, Jeollanam-do (KR); Ki-young Nam, Jeollanam-do (KR); Yong-yeon Hwang, Daejeon (KR); Je-sun Yoo, Gyeongsangbok-do (KR); Hyeon-gook Kim, Seoul (KR); Myeong-soo Song, Jeollanam-do (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/676,516

(22) PCT Filed: Aug. 29, 2008

(86) PCT No.: PCT/KR2008/005081
§ 371 (c)(1),
(2), (4) Date: Mar. 23, 2010

(87) PCT Pub. No.: WO2009/031787
PCT Pub. Date: Mar. 12, 2009

(65) Prior Publication Data
US 2010/0210773 A1    Aug. 19, 2010

(30) Foreign Application Priority Data

Sep. 5, 2007 (KR) .................. 10-2007-0089779
Jan. 4, 2008 (KR) .................. 10-2008-0001392
Jun. 27, 2008 (KR) .................. 10-2008-0061414

(51) Int. Cl.
*C08K 3/10* (2006.01)
*C08K 3/22* (2006.01)
*C09K 21/00* (2006.01)
*C07C 381/00* (2006.01)

(52) U.S. Cl. ........ 524/410; 252/601; 252/609; 524/394; 524/412; 524/430; 524/502; 524/504; 524/521; 568/56; 568/639; 568/645; 568/647; 570/206; 570/210

(58) Field of Classification Search .................. 252/609, 252/601; 524/410, 412, 504, 521, 101, 81, 524/466, 394, 430, 502; 570/184, 210, 206; 568/56, 639, 645, 647
See application file for complete search history.

(56) References Cited

U.S. PATENT DOCUMENTS

| 4,880,862 | A | | 11/1989 | Termine et al. |
| 5,039,729 | A | | 8/1991 | Brackenridge et al. |
| 5,055,235 | A | * | 10/1991 | Brackenridge et al. ........ 252/609 |
| 2007/0142524 | A1 | * | 6/2007 | Ryu et al. ..................... 524/394 |

FOREIGN PATENT DOCUMENTS

| KR | 2003-0035481 | * | 10/2001 |
| KR | 2003-0035481 | A | 5/2003 |
| KR | 10-2007-0064924 | A | 6/2007 |
| KR | 10-2008-0085137 | A | 9/2008 |

OTHER PUBLICATIONS

Korean Office Action dated Aug. 19, 2010 for Korean Application No. 10-2008-0061414.
Chinese Office Action dated May 19, 2011, for Chinese Application No. 200880105880.1.

* cited by examiner

*Primary Examiner* — Bijan Ahvazi
(74) *Attorney, Agent, or Firm* — Birch, Stewart, Kolasch & Birch, LLP

(57) ABSTRACT

The present invention provides a flame retardant resin composition comprising (A) 100 weight part of a basic resin comprising acrylonitrile-butadiene-styrene copolymer resin and styrene-acrylonitrile copolymer resin; and (B) 10-30 weight part of a bromine-based organic compound flame retardant, and selectively comprising (C) 1-20 weight part of an antimony-based auxiliary flame retardant and (D) 1-10 weight part of one or more compounds selected from the group consisting of metalstearate and stearamide compounds, wherein the bromine-based organic compound flame retardant (B) is octabromodiphenyl ethane. The flame retardant resin composition of the present invention has excellent flame retardancy, impact strength and melt flow index.

16 Claims, No Drawings

FLAME RETARDANT RESIN COMPOSITION HAVING GOOD IMPACT STRENGTH AND HIGH MELT FLOW INDEX

CROSS REFERENCE TO RELATED APPLICATIONS

The present application is a national phase entry under 35 U.S.C. 371 of International Application No. PCT/KR2008/005081, filed 29 Aug. 2008, which claims the benefit of Korean Patent Application No. 10-2007-0089779, filed 5 Sep. 2007; Korean Patent Application No. 10-2008-0001392, filed 4 Jan. 2008; and Korean Patent Application No. 10-2008-0061414, filed 27 Jun. 2008. The entire contents of all are hereby incorporated by reference into the present application.

TECHNICAL FIELD

The present invention relates to a flame retardant resin composition, more precisely a flame retardant resin composition having significantly improved impact strength and melt flow index along with excellent flame retardancy.

BACKGROUND ART

Acrylonitrile-Butadiene-Styrene (referred to as 'ABS', hereinafter) has been widely applied in electric appliances, electronic products and office automation machinery. However, this resin itself is not flame retardant. So, it is necessarily changed to flame retardant ABS resin by adding a flame retardant and an auxiliary flame retardant in order to endow flame retardancy to the resin.

However, when a flame retardant and a auxiliary flame retardant are added to ABS resin in order to improve flame retardancy, mechanical properties and physical properties of the resin including impact strength, melt flow index and elongation are significantly reduced.

That is, the flame retardant ABS resin produced with the addition of a flame retardant and auxiliary flame retardant is expected to have poor mechanical properties, particularly poor impact strength and melt flow index. Therefore, it is important to develop a flame retardant ABS resin having excellent physical properties.

As explained hereinbefore, a flame retardant necessarily added to a flame retardant ABS resin is a major cause of reducing mechanical properties of the resin. To overcome this problem, various additives and stabilizers can be tried to increase impact strength and melt flow index. However, the addition of expensive additives raises the prime cost and might reduce other physical properties of the resin.

Therefore, it is required to develop a novel flame retardant ABS resin having excellent impact strength, melt flow index and flame retardancy.

DISCLOSURE OF INVENTION

It is an object of the present invention, to overcome the above problems of the prior art, to provide a flame retardant resin composition with significantly improved impact strength, melt flow index along with excellent flame retardancy.

The above object and other objects of the present invention can be achieved by the following embodiments of the present invention.

The present invention is described in detail hereinafter.

To achieve the object, the present invention provides a flame retardant resin composition comprising:

(A) 100 weight part of a basic resin composed of acrylonitrile-butadiene-styrene copolymer resin and styrene-acrylonitrile copolymer resin; and (B) 10~30 weight part of a bromine based organic compound flame retardant, which is octabromodiphenyl ethane represented by formula 1.

[Chem. 1]

Chemistry Figure 1

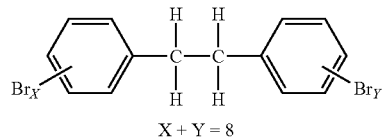

X + Y = 8

The flame retardant resin composition of the present invention can additionally include (C) 1~20 weight part of an antimony based auxiliary flame retardant; and (D) 1~10 weight part of one or more compounds selected from the group consisting of metal stearate and stearamide based compounds per 100 weight part of the basic resin.

The present invention provides a flame retardant resin composition comprising (A) a basic resin composed of acrylonitrile-butadiene-styrene copolymer resin and styrene-acrylonitrile copolymer resin; and (B) a bromine based organic compound flame retardant, which is octabromodiphenyl ethane represented by formula 1.

[Chemistry FIG. 1]

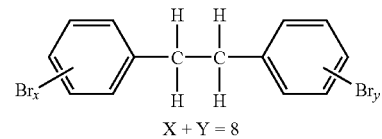

X + Y = 8

The flame retardant resin composition of the present invention can additionally include (C) an antimony based auxiliary flame retardant; and (D) one or more compounds selected from the group consisting of metalstearate and stearamide based compounds.

As for the flame retardant resin composition of the present invention, the basic resin of (A) is preferably composed of 10~90 weight % of an acrylonitrile-butadiene-styrene copolymer resin and 10~90 weight % of a styrene-acrylonitrile copolymer resin, and the styrene-acrylonitrile copolymer resin herein is preferably the resin having the molecular weight of 50,000~250,000 and an acrylonitrile monomer of 20~40 weight %. The acrylonitrile-butadiene-styrene copolymer resin herein can be prepared by any conventional polymerization methods, preferably by emulsion graft polymerization. Particularly, the acrylonitrile-butadiene-styrene copolymer resin is preferably composed of 10~90 weight % of the acrylonitrile-butadiene-styrene copolymer resin prepared by emulsion graft polymerization (butadiene rubber content: 30~70 weight %) and 10~90 weight % of the acrylonitrile-butadiene-styrene copolymer prepared by bulk graft polymerization (butadiene rubber content: 2~20 weight %). The mixed resin comprising the two resins each prepared by emulsion polymerization and bulk polymerization favors the increase of impact strength and elongation, compared with the use of single resin.

The acrylonitrile-butadiene-styrene copolymer resin prepared by emulsion graft polymerization preferably contains a styrene monomer by 20~65 weight % and an acrylonitrile monomer by 5~40 weight %. The acrylonitrile-butadiene-styrene copolymer resin prepared by bulk graft polymerization preferably contains a styrene monomer by 50~80 weight % and an acrylonitrile monomer by 10~30 weight %. The preferable mean diameter of butadiene rubber particles used for emulsion graft polymerization to prepare acrylonitrile-butadiene-styrene copolymer is 0.1~0.5 µm, while the preferable mean diameter of butadiene rubber particles used for bulk graft polymerization to produce the same is 1~5 µm. In particular, the butadiene rubber used for the bulk graft polymerization to prepare acrylonitrile-butadiene-styrene copolymer is preferably styrene-butadiene block copolymer containing styrene by 3~50 weight %.

In the meantime, the basic resin (A) of the present invention can also be composed of (a) 5~50 weight part of an acrylonitrile-butadiene-styrene copolymer resin prepared by emulsion graft polymerization; (b) 5~50 weight part of an acrylonitrile-butadiene-styrene copolymer resin prepared by bulk graft polymerization; and (c) 90~10 weight part of styrene-acrylonitrile copolymer resin.

Even in the case that the acrylonitrile-butadiene-styrene copolymer resin produced by emulsion polymerization alone is used as the resin of the present invention; it can still comprise the above composition. In the case that the resin of the present invention is the acrylonitrile-butadiene-styrene copolymer resin prepared by bulk graft polymerization, impact strength of the composition of the invention can be increased but melt flow index is reduced. So, according to a target property, either emulsion polymerization or bulk polymerization is selected to prepare the copolymer or both copolymers prepared by the two methods can be properly mixed.

The above composition favors the improvement of impact strength and melt flow index of the final product.

Such polymers compositing the basic resin can be prepared as follows.

One of the constituents of the basic resin, (a) the acrylonitrile-butadiene-styrene copolymer resin prepared by emulsion graft polymerization can be prepared by emulsion polymerization by adding 30~70 weight part of butadiene rubber of 0.1~0.5 µm in mean diameter, 5~40 weight part of acrylonitrile monomer and 2065 weight part of styrene monomer stepwise or as a package in the presence of 0.6~2 weight part of an emulsifying agent, 0.2~1 weight part of a molecular weight regulator, and 0.05~0.5 weight part of a polymerization initiator. The prepared acrylonitrile-butadiene-styrene copolymer resin latex can be prepared as powders by the processes of coagulation with 5% sulfuric acid solution and drying.

The acrylonitrile-butadiene-styrene copolymer resin (b) prepared by bulk graft polymerization, the other constituent of the basic resin, can be prepared by graft-copolymerization as follow. 2~20 weight part of styrene-butadiene block copolymer rubber, 50~80 weight part of styrene monomer, 10~30 weight part of acrylonitrile monomer and 10~60 weight part of ethylbenzene are added to the reactor serially or at a time. 0.01~0.2 weight part of a polymerization initiator is added thereto. The reaction mixture is loaded in the continuous polymerizing apparatus equipped with 4 stirring reactors in series, wherein the concentration of acrylonitrile monomer, graft ratio and stirring speed are regulated. Any conventional polymerization initiator can be used as the polymerization initiator herein. As an example, 1,1-bis(t-butyl peroxy)-3,3,5-trimethyl cyclohexane can be used.

The styrene-acrylonitrile copolymer, one of the constituents of the basic resin, can be prepared by the conventional polymerization method such as emulsion polymerization or bulk polymerization with styrene monomer and acrylonitrile monomer.

Hereinbefore, single compounds such as styrene, butadiene and acrylonitrile were mentioned as the monomers for the basic resin, but it is well understood by those in the art that their derivatives can be used as monomers for the basic resin as well. Therefore, styrene, butadiene and acrylonitrile monomers in this description include their derivatives having substituents.

To prepare the flame retardant resin composition of the present invention, octabromodiphenyl ethane is characteristically used as a bromine-based flame retardant (B). The flame retardant resin compositions containing bromine-based flame retardants such as tetrabromobisphenol A, brominated epoxy oligomer, hexabromodiphenoxy ethane and decabromodiphenyl ethane have been confirmed to have improved weatherability and thermo-stability. The flame retardant resin compositions containing bromine-based flame retardants are described in Korean Patent Publication Nos. 2007-64924, 2005-74062, 2004-47218, 2003-35481 and 2002-53197.

Octabromodiphenyl ethane used as a basic flame retardant in this invention is the compound that includes 8 bromines in one molecule. It is very difficult to obtain pure octabromodiphenyl ethane by the conventional preparation method, and it is also very difficult to purify thereof. In the present invention, octabromodiphenyl ethane was not highly purified. Instead, a mixture containing octabromodiphenyl ethane as a major component was used. Octabromodiphenyl ethane used in this invention preferably has 7.5~8 bromines in one molecule, preferably 8 bromines in one molecule, and can include every isomer that contains 8 bromines. The range of melting point of this compound is very wide because of many isomers, which is 150~250° C. The lowest cut of the melting point is at least 150° C., preferably between 180-200° C., and the highest cut of the melting point is up to 250° C., preferably 210-230° C. The preferable melting point of the compound used in this invention is 190~220° C. The above range of melting point is significantly low, compared with that of decabromodiphenyl ethane whose melting point is 350° C. So, octabromodiphenyl ethane is melted and evenly dispersed in the resin during the processing into a flame retardant resin. Therefore, the present inventors succeeded in the development of a novel flame retardant resin composition having excellent physical properties including melt flow index and impact strength, compared with the flame retardant resins prepared by using decabromodiphenyl ethane, and retaining weatherability and thermo-stability, the advantages that can be provided by decabromodiphenyl ethane, by using octabromodiphenyl ethane as a flame retardant.

As explained hereinbefore, octabromodiphenyl ethane is included in the flame retardant resin composition of the present invention as a bromine-based flame retardant. If the content of octabromodiphenyl ethane in 100 weight part of the basic resin is up to 10 weight part, flame retardancy is reduced. On the other hand, if the content is at least 30 weight part, physical properties of the flame retardant resin are reduced. Therefore, the preferable content of octabromodiphenyl ethane, to improve flame retardancy, processiblity, and other mechanical properties, is 10~30 weight part.

As one of the additives that can be added to the flame retardant resin composition of the present invention, the antimony-based auxiliary flame retardant (C) is functioning to improve flame retardancy together with the bromine-based organic compound flame retardant (B), which is exemplified by antimony trioxide, antimony pentoxide, metal antimony and antimony trichloride, etc. And, antimony trioxide is preferably used. Mean diameter of the antimony trioxide is 0.02~5 μm preferably up to 0.5 μm so as to secure high impact strength. The antimony-based auxiliary flame retardant (C) is preferably added by 1~20 weight part per 100 weight part of the basic resin. The content in the above range was judged to be effective in helping the flame retardant be full functioning to increase flame retardancy without reducing any physical properties of the final product.

As one of the additives that can be added to the flame retardant resin composition of the present invention, the metalstearate and steramide compounds (D) are functioning as a lubricant that can increase melt flow index of the product, resulting in improvement of physical properties of the product. The metalstearate compound herein can be one or more compounds selected from the group consisting of calciumstearate, magnesiumstearate, sodiumstearate, zincstearate, bariumstearate and aluminum-stearate. The steramide compound herein can be ethylene bis steramide. The preferable content of the metalstearate and steramide compounds (D) is 1~10 weight part per 100 weight part of the basic resin. When the above compounds are added by the above content, processability and other physical properties of the product can be improved.

The flame retardant resin composition comprising the above components is the acrylonitrile-butadiene-styrene resin composition that is prepared by adding a bromine-based organic compound flame retardant to the basic resin composed of acrylonitrile-butadiene-styrene copolymer resin and styrene-acrylonitrile copolymer resin prepared by emulsion graft polymerization and bulk graft polymerization and selectively adding an antimony-based auxiliary flame retardant to increase thermo-stability and weatherability and also selectively adding one or more compounds selected from the group consisting of metalstearate and steramide compounds to increase other physical properties.

The flame retardant resin composition of the present invention can additionally include one or more impact modifiers selected from the group consisting of chlorinated polyethylene, polybutadiene polymer, styrene-butadiene-styrene copolymer, styrene-ethylene-butadiene-styrene copolymer, styrene-ethylene-propylene-styrene copolymer, thermoplastic polyurethane, polybutyleneterephthalate, ethylene-vinyl-acetate copolymer, styrene-isoprene-styrene copolymer and dialkylpolysiloxane by 1~15 weight part per 100 weight part of the basic resin.

The flame retardant resin composition of the present invention can also include other additives such as a lubricant, a heat stabilizer, an anti-dripping agent, an anti-oxidant, a photostabilizer, a UV blocking agent, a pigment or an inorganic filler, etc. The preferable contents of such additives in 100 weight part of the basic resin are as follows; a fluorine-based compound used as an anti-dripping agent is preferably added by 0.05~2 weight part, a lubricant is added by 0.2~10 weight part and a stabilizer is added by 0.2~10 weight part.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES AND COMPARATIVE EXAMPLES

Example 1

To 100 weight part of the basic resin (A) composed of (a) 33 weight part of ABS copolymer resin including 60 weight % of butadiene rubber of 0.3 μm in mean diameter, 30 weight % of styrene monomer and 10 weight % of acrylonitrile monomer and (c) 67 weight part of styrene-acrylonitrile copolymer resin having the weight average molecular weight of 120,000 and including 24 weight % of acrylonitrile monomer prepared by emulsion graft polymerization, were added 15 weight part of a bromine-based organic compound, octabromodiphenyl ethane (B), 5 weight part of antimony trioxide of 0.35 μm in mean diameter (C), 2 weight part of ethylene bis steramide (EBA), a steramide lubricant (D), and additionally 0.07 weight part of an anti-dripping agent, 0.3 weight part of an anti-oxidant, 0.3 weight part of a thermostabilizer, 0.3 weight part of magnesium stearate, and 0.1 weight part of dimethylpolysiloxane. The mixture was well mixed using a Hansel mixer, followed by extrusion using a twin screw extruder to give a pellet type resin composition. Flame retardancy and physical property test samples were prepared with the pellet by injection molding.

The octabromodiphenyl ethane used in this invention has 7.5~8.5 bromines in one molecule prepared by bromination of diphenyl ethane. Particularly, diphenyl ethane was dissolved in the solvent inactive to the reaction (halogenated hydrocarbon solvent, methylene bromide, methylene chloride, chloroform, etc) in the presence of a Lewis acid catalyst (ferrous compound, zirconium tetrachloride, aluminum trichloride, antimony trioxide, etc), to which brominating material (bromine, bromine chloride, etc) was added. Upon completion of the reaction, the produced slurry was purified and dried.

Example 2

An experiment was performed by the same manner as described in Example 1 except that 100 weight part of the basic resin (A) composed of (a) 33 weight part of ABS copolymer resin including 60 weight % of butadiene rubber of 0.3 μm in mean diameter, 30 weight % of styrene monomer and 10 weight % of acrylonitrile monomer prepared by emulsion graft polymerization, (b) 10 weight part of ABS copolymer resin including 13 weight % of butadiene rubber of 0.1 μm in mean diameter, 70 weight % of styrene monomer and 17 weight % of acrylonitrile monomer prepared by bulk graft polymerization and (c) 57 weight part of styrene-acrylonitrile copolymer resin having the weight average molecular weight of 120,000 and 24 weight % of acrylonitrile monomer was used.

Example 3

An experiment was performed by the same manner as described in Example 1 except that 4 weight part of chlorinated polyethylene was additionally added as an impact modifier.

Example 4

An experiment was performed by the same manner as described in Example 2 except that 4 weight part of chlorinated polyethylene was additionally added as an impact modifier.

Comparative Example 1

To 100 weight part of the basic resin (A) composed of (a) 33 weight part of ABS copolymer resin comprising 60 weight % of butadiene rubber of 0.3 μm in mean diameter, 30 weight % of styrene monomer and 10 weight % of acrylonitrile monomer and (c) 67 weight part of styrene-acrylonitrile copolymer resin having the weight average molecular weight of 120,000 and 24 weight % of acrylonitrile monomer prepared by emulsion graft polymerization were added 15 weight part of a bromine-based organic compound flame retardant, decabromodiphenyl ethane (FM2100, Great Lakes, USA) (B), 5 weight part of antimony trioxide of 0.35 μm in mean diameter (C), 2 weight part of ethylene bis steramide (EBA), a steramide lubricant (D), and additionally 0.07 weight part of an anti-dripping agent, 0.3 weight part of an anti-oxidant, 0.3 weight part of a thermo-stabilizer, 0.3 weight part of magnesium stearate, and 0.1 weight part of dimethylpolysiloxane. The mixture was well mixed using a Hansel mixer, followed by extrusion using a twin screw extruder to give a pellet type resin composition. Flame retardancy and physical property test samples were prepared with the pellet by injection molding.

Comparative Example 2

An experiment was performed by the same manner as described in Comparative Example 1 except that 100 weight part of the basic resin (A) composed of (a) 33 weight part of ABS copolymer resin including 60 weight % of butadiene rubber of 0.3 μm in mean diameter, 30 weight % of styrene monomer and 10 weight % of acrylonitrile monomer prepared by emulsion graft polymerization, (b) 10 weight part of ABS copolymer resin including 13 weight % of butadiene rubber of 0.1 μm in mean diameter, 70 weight % of styrene monomer and 17 weight % of acrylonitrile monomer prepared by bulk graft polymerization and (c) 57 weight part of styrene-acrylonitrile copolymer resin having the weight average molecular weight of 120,000 and 24 weight % of acrylonitrile monomer was used.

Comparative Example 3

An experiment was performed by the same manner as described in Comparative Example 1 except that 4 weight part of chlorinated polyethylene was additionally added as an impact modifier.

Comparative Example 4

An experiment was performed by the same manner as described in Comparative Example 2 except that 4 weight part of chlorinated polyethylene was additionally added as an impact modifier.

Comparative Example 5

An experiment was performed by the same manner as described in Example 1 except that a mixture of polybromodiphenyl ethane was used as the bromine-based flame retardant. The bromine-based flame retardant of polybromodiphenyl ethane mixture was prepared by brominating diphenyl ethane, thereby containing seven brome atoms per one molecule. Conventionally, diphenyl ethane was dissolved in a nonreactive solvent (halogenated hydrocarbon solvent, brominated methylene, methylene chloride, chloroform, etc.) in the presence of Lewis acid catalyst (ferrous compounds, zirconium tetrachloride, aluminum trichloride, antimony trichloride, etc.) and bromine source (bromine, bromochloride, etc.) was reacted with dripping to produce slurry. The slurry was purified, dried and used. A flame retardant has melting points ranging from 110° C. to 180° C. and contains compounds having bromine atoms of which the number is from five to ten.

TABLE 1

|  | Example | | | | Comparative Example | | | | |
| --- | --- | --- | --- | --- | --- | --- | --- | --- | --- |
|  | 1 | 2 | 3 | 4 | 1 | 2 | 3 | 4 | 5 |
| Emulsion ABS | 33 | 33 | 33 | 33 | 33 | 33 | 33 | 33 | 33 |
| SAN | 67 | 57 | 67 | 57 | 67 | 57 | 67 | 57 | 67 |
| Bulk ABS | — | 10 | — | 10 | — | 10 | — | 10 | — |
| Bromine-based flame retardant | 15 | 15 | 15 | 15 | 15 | 15 | 15 | 15 | 15 |
| Antimony-based auxiliary flame retardant | 5 | 5 | 5 | 5 | 5 | 5 | 5 | 5 | 5 |
| Lubricant | 2 | 2 | 2 | 2 | 2 | 2 | 2 | 2 | 2 |
| Impact modifier | — | — | 4 | 4 | — | — | 4 | 4 | — |

Physical properties of the acrylonitrile-butadiene-styrene resin composition samples prepared in the above examples and comparative examples were measured by the following methods and the results are shown in Table 2.

(1) Impact strength: Impact strength was tested by ASTM D256. Evaluation was made for ⅛ inch thickness and the unit was Kg?cm/cm.

(2) Tensile strength: Tensile strength was tested by ASTM D638 under the condition of 50 mm/min and the unit was Kg/cm2.

(3) Melt flow index: Melt flow index was tested by ASTM D1238 at 220° C. with the weight of 10 kg. The unit was g/10 min.

(4) Weatherability: ΔE was measured after leaving the plate samples in a UV sterilizer for 6 hours.

(5) Flame retardancy: Flame retardancy was measured according to the test standard of UL-94.

TABLE 2

| Physical property | Example | | | | Comparative Example | | | | |
| --- | --- | --- | --- | --- | --- | --- | --- | --- | --- |
|  | 1 | 2 | 3 | 4 | 1 | 2 | 3 | 4 | 5 |
| Impact strength (Kg · cm/cm) | 21.1 | 25.5 | 24.6 | 29.0 | 13.8 | 16.1 | 15.9 | 20.2 | 21.3 |
| Tensile strength (Kg/cm$^2$) | 376 | 360 | 372 | 355 | 370 | 348 | 373 | 356 | 362 |
| Melt flow index (g/10 min) | 64.4 | 52.1 | 61.2 | 49.0 | 36.1 | 30.7 | 38.7 | 29.5 | 65.2 |

TABLE 2-continued

| Physical property | Example | | | | Comparative Example | | | | |
|---|---|---|---|---|---|---|---|---|---|
| | 1 | 2 | 3 | 4 | 1 | 2 | 3 | 4 | 5 |
| Weatherability (5 hrs; ΔE) | 2.34 | 2.14 | 2.40 | 2.28 | 2.28 | 2.08 | 2.34 | 2.15 | 3.81 |
| Flame retardancy (1/12") | V0 | V0 | V0 | V0 | V0 | V0 | V2 | V2 | V2 |

As shown in Table 2, the acrylonitrile-butadiene-styrene resin compositions of Examples 1-4 were confirmed to have excellent impact strength, melt flow index and flame retardancy, compared with the acrylonitrile-butadiene-styrene resin compositions of Comparative Examples 1?5.

The compositions of Examples 3~4 containing octabromodiphenyl ethane as a bromine-based organic compound flame retardant and chlorinated polyethylene as an impact modifier showed excellent flame retardancy, impact strength and melt flow index, compared with the compositions of Comparative Examples 3~4 produced containing decabromodiphenyl ethane and chlorinated polyethylene. Also, the composition of Example 2 containing bulk ABS prepared by bulk graft polymerization and added with octabromodiphenyl ethane as a flame retardant showed significantly improved impact strength and melt flow index, compared with the composition of comparative example 2 containing bulk ABS and added with decabromodiphenyl ethane as a flame retardant. The above results indicate that the addition of octabromodiphenyl ethane as a flame retardant can improve various physical properties even in the basic resin containing bulk ABS. Weatherability of the composition containing octabromodiphenyl ethane as a flame retardant was as good as that of the composition containing decabromodiphenyl ethane known as an excellent water-resistant flame retardant, suggesting that octabromodiphenyl ethane is good enough to take the place of decabromodiphenyl ethane.

In addition, Comparative Example 5 in which flame retardant of polybromodiphenyl ethane having seven bromine atoms on the average per one molecule exhibited similar properties to, however lower weatherability and flame retardancy (decreased from V0 to V2) than Example 1 in which the components were same as Comparative Example 5 except that octabromodiphenyl ethane was used as a flame retardant. This is because the number of bromine atom in octabromodiphenyl ethane of Example 1 is more than that of Comparative Example 5 and weatherability of octabromodiphenyl ethane is better than that of polybromodiphenyl ethane.

Example 5

An experiment was performed by the same manner as described in Example 1, except that the bromine-based organic compound flame retardant (B) composed of 10 weight part of octabromodiphenyl ethane (a) and 5 weight part of tetrabromobisphenol A (b) (CP-2000, average melting point: 181° C., Albermarle, USA) known as a melt type flame retardant was used.

Example 6

An experiment was performed by the same manner as described in Example 1, except that the bromine-based organic compound flame retardant (B) composed of 10 weight part of octabromodiphenyl ethane (a) and 5 weight part of brominated epoxy oligomer (b) (CXB-6005, average softening point: 91° C., Woojin Copolymer Co., Korea) known as a melt type flame retardant was used.

Example 7

An experiment was performed by the same manner as described in Example 1, except that the bromine-based organic compound flame retardant (B) composed of 10 weight part of octabromodiphenyl ethane (a) and 5 weight part of 2,4,6-Tris(2,4,6-tribromophenoxy)-1,3,5-triazine (SR-245, average melting point: 227° C., Dai-Ichi Kogyo Seiyaku, Japan) known as a melt type flame retardant was used.

Example 8

An experiment was performed by the same manner as described in Example 1, except that the bromine-based organic compound flame retardant (B) composed of 10 weight part of octabromodiphenyl ethane (a) and 5 weight part of decabromodiphenyl ethane (b) (FM2100, the same product as the one used in Comparative Example 1) was used.

Comparative Example 6

An experiment was performed by the same manner as described in Comparative Example 1, except that the bromine-based organic compound flame retardant (B) composed of 10 weight part of decabromodiphenyl ethane (a) (FM2100, the same product as the one used in Comparative Example 1) and 5 weight part of tetrabromo-bisphenol A (b) (CP-2000, Albermarle, USA, average melting point: 181° C.) known as a melt type flame retardant was used.

Comparative Example 7

An experiment was performed by the same manner as described in Comparative Example 1, except that the bromine-based organic compound flame retardant (B) composed of 5 weight part of octabromodiphenyl ethane (a) and 10 weight part of tetrabromobisphenol A (b) (CP-2000, Albermarle, USA, average melting point: 181° C.) known as a melt type flame retardant was used.

Comparative Example 8

An experiment was performed by the same manner as described in Comparative Example 1, except that the bromine-based organic compound flame retardant (B) composed of 15 weight part of tetrabromobisphenol A (b) (CP-2000, Albermarle, USA, average melting point: 181° C.) known as a melt type flame retardant was used.

Comparative Example 9

An experiment was performed by the same manner as described in Comparative Example 1, except that the bromine-based organic compound flame retardant (B) composed of 21 weight part of tetrabromobisphenol A (b) (CP-2000, Albermarle, USA, average melting point: 181° C.) known as a melt type flame retardant was used.

TABLE 3

|  | | Example | | | | Comparative Example | | | |
|---|---|---|---|---|---|---|---|---|---|
|  | | 5 | 6 | 7 | 8 | 6 | 7 | 8 | 9 |
| Emulsion ABS | | 33 | 33 | 33 | 33 | 33 | 33 | 33 | 33 |
| SAN | | 67 | 67 | 67 | 67 | 67 | 67 | 67 | 67 |
| Bromine- | Octa | 10 | 10 | 10 | 10 | — | 5 | — | — |
| based flame retardant (a) | Deca | — | — | — | 5 | 10 | — | — | — |
| Bromine-based flame retardant (b) | | 5 | 5 | 5 | — | 5 | 10 | 15 | 21 |
| Antimony-based auxiliary flame retardant | | 5 | 5 | 5 | 5 | 5 | 5 | 5 | 5 |
| Lubricant | | 2 | 2 | 2 | 2 | 2 | 2 | 2 | 2 |

TABLE 4

|  | Example | | | | Comparative Example | | | |
|---|---|---|---|---|---|---|---|---|
|  | 5 | 6 | 7 | 8 | 6 | 7 | 8 | 9 |
| Impact strength (Kg · cm/cm) | 21.8 | 22.5 | 23.8 | 19.3 | 14.9 | 19.1 | 15.3 | 12.6 |
| Tensile strength (Kg/cm$^2$) | 387 | 379 | 377 | 371 | 380 | 397 | 399 | 402 |
| Melt flow index (g/10 min) | 69.7 | 67.6 | 65.6 | 51.9 | 45.4 | 84.3 | 91.0 | 131.3 |
| Weatherability (5 hrs; ΔE) | 3.51 | 2.74 | 2.23 | 2.78 | 3.48 | 4.58 | 4.82 | 5.33 |
| Flame retardancy (1/12") | V0 | V0 | V0 | V0 | V0 | V2 | burning | V0 |

As shown in Table 4, in examples 5?8, octabromodiphenyl ethane was partially substituted with other bromine-based flame retardants and as a result it was confirmed that weatherability and flame retardancy were maintained and impact strength and melt flow index were improved.

In particular, 5 weight part of octabromodiphenyl ethane was substituted with tetra-bromobisphenol A, a melt type flame retardant, in Example 5. As a result, the composition was confirmed to have excellent physical properties, compared with the composition of Comparative Example 6 wherein the equal weight part of decabromodiphenyl ethane was substituted with tetrabromobisphenol A. In the meantime, the compositions in which most or whole amount of octabromodiphenyl ethane was substituted with tetrabromobisphenol A, prepared in Comparative Examples 7~9, exhibited improvement of melt flow index but decrease of other properties including flame retardancy, weatherability and impact strength.

Therefore, Examples 5~8 proved that partial substitution of octabromodiphenyl ethane with other bromine-based flame retardants can improve impact strength and melt flow index with maintaining weatherability and flame retardancy.

INDUSTRIAL APPLICABILITY

As explained hereinbefore, the flame retardant resin composition of the present invention has not only excellent flame retardancy but also excellent impact strength and melt flow index.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A flame retardant resin composition comprising:
   (A) 100 parts by weight of a basic resin composed of acrylonitrile-butadiene-styrene copolymer and styrene-acrylonitrile copolymer and
   (B) 10-30 parts by weight of a bromine-based organic flame retardant compound, wherein the bromine-based organic flame retardant compound (B) contains octabromodiphenyl ethane represented by the following formula 1 and is a mixture containing 7.5-8.5 bromines at average in one molecule thereof, produced by brominating diphenylethane, and has a lowest melting point of 180-200° C. and a highest melting point of 210-230° C., and
   wherein the flame retardant resin composition has a flame retardancy of V0 according to UL-94 and an impact strength of 19.3 to 29.0 kg.cm/cm,
   wherein flame retardancy of the flame retardant resin composition is V-2 according to UL-94

[Formula 1]

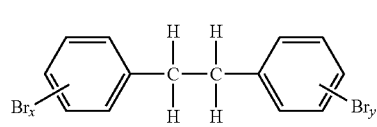

wherein X+Y=8,
wherein the basic resin (A) is composed of 10-90 weight % of the acrylonitrile-butadiene-styrene copolymer and 10-90 weight % of the styrene-acrylonitrile copolymer, and the styrene-acrylonitrile copolymer has a weight average molecular weight of 50,000-250,000 and has an acrylonitrile monomer by 20-40 weight %, wherein the acrylonitrile-butadiene-styrene copolymer is composed of 10-90 weight % of the acrylonitrile-butadiene-styrene copolymer prepared by emulsion graft polymerization and has butadiene rubber content of 30-70 weight % and 10-90 weight % of the acrylonitrile-butadiene-styrene copolymer prepared by bulk graft polymerization and has butadiene rubber content of 2-20 weight %.

2. The flame retardant resin composition according to claim 1, wherein the acrylonitrile-butadiene-styrene copolymer prepared by emulsion graft polymerization is composed of 20-65 weight % of a styrene monomer and 5-40 weight % of an acrylonitrile monomer, and the acrylonitrile-butadiene-styrene copolymer prepared by bulk graft polymerization is composed of 50-80 weight % of a styrene monomer and 10-30 weight % of an acrylonitrile monomer.

3. The flame retardant resin composition according to claim 2, wherein the mean diameter of butadiene rubber particles used for emulsion graft polymerization to prepare the acrylonitrile-butadiene-styrene copolymer is 0.1-0.5 µm, and the mean diameter of butadiene rubber particles used for bulk graft polymerization to prepare the acrylonitrile-butadiene-styrene copolymer is 1-5 µm.

4. The flame retardant resin composition according to claim 3, wherein the butadiene rubber used for bulk graft polymerization to prepare the acrylonitrile-butadiene-styrene copolymer is styrene-butadiene block copolymer rubber containing styrene by 3-50 weight %.

5. The flame retardant resin composition according to claim 1, wherein the composition additionally includes 1-20 parts by weight of an antimony-based auxiliary flame retardant (C) per 100 parts by weight of the basic resin.

6. The flame retardant resin composition according to claim 5, wherein the antimony-based auxiliary flame retardant (C) is one or more compounds selected from the group consisting of antimony trioxide, antimony pentoxide, metal antimony and antimony trichloride.

7. The flame retardant resin composition according to claim 5, wherein the antimony-based auxiliary flame retardant (C) is antimony trioxide having 0.02-5 µm in mean diameter.

8. The flame retardant resin composition according to claim 1, wherein the composition additionally includes 1-10 parts by weight of one or more compounds (D) selected from the group consisting of metalstearate and steramide compounds per 100 parts by weight of the basic resin.

9. The flame retardant resin composition according to claim 8, wherein the metalstearate compound (D) is one or more compounds selected from the group consisting of calciumstearate, magnesiumstearate, sodiumstearate, zincstearate, bariumstearate and aluminumstearate, and the steramide compound is ethylene bis steramide.

10. The flame retardant resin composition according to claim 1, wherein the composition additionally includes 1-15 parts by weight of one or more impact modifiers selected from the group consisting of chlorinated polyethylene, polybutadiene polymer, styrene-butadiene-styrene copolymer, styrene-ethylene-butadiene-styrene copolymer, styrene-ethylene-propylene-styrene copolymer, thermoplastic polyurethane, polybutyleneterephthalate, ethylene-vinyl-acetate copolymer, styrene-isoprene-styrene copolymer and dialkylpolysiloxane by 1-15 parts by weight per 100 parts by weight of the basic resin.

11. The flame retardant resin composition according to claim 1, wherein the composition additionally includes one or more additives selected from the group consisting of a lubricant, a heat stabilizer, an anti-dripping agent, an anti-oxidant, a photo-stabilizer, a UV blocking agent, a pigment and an inorganic filler.

12. The flame retardant resin composition according to claim 1, wherein the weight ratio of octabromodiphenyl ethane to one or more bromine-based flame retardants selected from the group consisting of tetrabromobisphenol A, brominated epoxy oligomer, hexabromodiphenoxy ethane, bis(tribromophenoxy)ethane, brominated polystyrene and 2,4,6,-Tris(2,4,6-tribromophenoxy)-1,3,5-triazine, decabromodiphenyl ethane, is 1:10-10:1.

13. The flame retardant resin composition according to claim 12, wherein the octabromodiphenyl ethane has the melting point of 150-250° C.

14. The flame retardant resin composition according to claim 1, wherein the octabromodiphenyl ethane has the melting point of 150-250° C.

15. The flame retardant resin composition according to claim 1, wherein the acrylonitrile-butadiene-styrene copolymer is prepared by emulsion graft polymerization and comprises 30-70 weight % of a butadiene rubber, 20-65 weight % of a styrene monomer and 5-40 weight % of an acrylonitrile monomer.

16. The flame retardant resin composition according to claim 1, wherein the bromine-based organic flame retardant compound has a lowest melting point of 180-200° C., and the flame retardant resin composition further comprises one or more compounds selected from the group consisting of metalstearate and steramide compounds.

\* \* \* \* \*